United States Patent
Govari

(10) Patent No.: US 12,257,042 B2
(45) Date of Patent: *Mar. 25, 2025

(54) LOCATION PAD FOR NEUROSURGICAL PROCEDURES

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 0 days.

This patent is subject to a terminal disclaimer.

(21) Appl. No.: 18/082,755

(22) Filed: Dec. 16, 2022

(65) Prior Publication Data

US 2023/0124397 A1    Apr. 20, 2023

Related U.S. Application Data

(63) Continuation of application No. 16/729,556, filed on Dec. 30, 2019, now Pat. No. 11,589,770.

(51) Int. Cl.
| | | |
|---|---|---|
| *A61B 5/00* | (2006.01) | |
| *A61B 5/06* | (2006.01) | |
| *A61B 34/20* | (2016.01) | |
| *G01R 33/385* | (2006.01) | |

(52) U.S. Cl.
CPC ............ *A61B 5/062* (2013.01); *A61B 5/065* (2013.01); *A61B 5/6868* (2013.01); *A61B 34/20* (2016.02); *G01R 33/385* (2013.01); *A61B 2034/2051* (2016.02); *A61B 2034/2072* (2016.02)

(58) Field of Classification Search
CPC ....... A61B 5/062; A61B 5/065; A61B 5/6868; A61B 34/20; A61B 2034/2051; A61B 2034/2072; A61B 2017/0092; A61B 2090/376; A61B 6/547; A61B 6/0442; G01R 33/385

See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |

(Continued)

FOREIGN PATENT DOCUMENTS

| | | |
|---|---|---|
| JP | 2017-012760 A | 1/2017 |
| WO | WO 1996/005768 A1 | 2/1996 |

OTHER PUBLICATIONS

European Communication dated Dec. 11, 2023, for Application No. 20829660.8, 5 pages.

(Continued)

*Primary Examiner* — Joel Lamprecht
(74) *Attorney, Agent, or Firm* — Frost Brown Todd LLP

(57) ABSTRACT

A location pad includes multiple field-generators and a frame. The multiple field-generators are configured to generate respective magnetic fields in a region-of-interest of a patient organ, so as to measure a position of a medical instrument in the region-of-interest. The frame is transparent to an X-ray radiation, and is configured to fix the multiple field-generators at respective positions surrounding the region-of-interest.

20 Claims, 2 Drawing Sheets

(56) References Cited

U.S. PATENT DOCUMENTS

| | | | |
|---|---|---|---|
| 6,690,963 B2 | 2/2004 | Ben-Haim et al. | |
| 9,326,702 B2 | 5/2016 | Eichler et al. | |
| 11,193,795 B2 | 12/2021 | Foster et al. | |
| 11,589,770 B2 * | 2/2023 | Govari | G01R 33/385 |
| 2002/0065455 A1 | 5/2002 | Ben-Haim et al. | |
| 2003/0120150 A1 | 6/2003 | Govari | |
| 2004/0068178 A1 | 10/2004 | Chang et al. | |
| 2006/0025668 A1 | 2/2006 | Peterson et al. | |
| 2007/0265526 A1 | 11/2007 | Govari et al. | |
| 2014/0275998 A1 | 9/2014 | Eichler et al. | |
| 2017/0007155 A1 | 1/2017 | Gliner | |
| 2017/0188882 A1 | 7/2017 | Foster et al. | |
| 2019/0056242 A1 | 2/2019 | Foster et al. | |
| 2019/0083115 A1 | 3/2019 | Bar-tal | |
| 2021/0196145 A1 | 7/2021 | Govari | |

OTHER PUBLICATIONS

International Search Report and Written Opinion dated Mar. 16, 2021, for International Application No. PCT/IB2020/061561, 13 pages.

Japanese First Office Action dated Apr. 16, 2024, for Application No. 2022-540511, 3 pages.

Japanese Final Office Action dated Oct. 22, 2024, for Application No. 2022-540511, 3 pages.

* cited by examiner

LOCATION PAD FOR NEUROSURGICAL PROCEDURES

This application is a continuation of U.S. patent application Ser. No. 16/729,556, filed Dec. 30, 2019, issued as U.S. Pat. No. 11,589,770, on Feb. 28, 2023, which is incorporated by reference as if fully set forth.

FIELD OF THE INVENTION

The present invention relates generally to medical devices, and specifically to location pads of magnetic position tracking systems used in neurosurgical procedures.

BACKGROUND OF THE INVENTION

Magnetic position tracking systems are used in a wide range of medical applications, such as in minimally invasive procedures. Examples of prior art techniques are provided below.

U.S. Patent application publication 2017/0007155, now abandoned, describes a location pad of a magnetic position tracking system. The location pad includes multiple field-generators and a frame. The field-generators are configured to generate respective magnetic fields in a region-of-interest of a patient body, for measuring a position of a medical instrument in the region-of-interest. The frame is configured to fix the multiple field-generators at respective positions surrounding the region-of-interest. The frame is open on at least one side of the region-of-interest.

U.S. Patent application publication 2014/0275998, now issued as U.S. Pat. No. 9,326,702 on May 3, 2016, describes a system for navigating a medical device including a magnetic field generator assembly that generates a magnetic field. Position sensors on the medical device, on an imaging system and on the body generate signals indicative of the positions within the magnetic field. The generator assembly and reference sensors are arranged such that a correlation exists between them and the positions of the body and of a radiation emitter and a radiation detector of the imaging system. An electronic control unit (ECU) determines, responsive to signals generated by the sensors, a position of the medical device, a position of one of the radiation emitter and detector and a distance between the emitter and detector.

SUMMARY OF THE INVENTION

An embodiment of the present invention that is described herein provides a location pad including multiple field-generators and a frame. The multiple field-generators are configured to generate respective magnetic fields in a region-of-interest of a patient organ, so as to measure a position of a medical instrument in the region-of-interest. The frame is transparent to an X-ray radiation, and is configured to fix the multiple field-generators at respective positions surrounding the region-of-interest.

In some embodiments, the field-generators include at least first and second field-generators, and the location pad includes at least a first electrical cable connected to the first field-generator, and a second electrical cable connected to the second field-generator, and the first and second electrical cables are positioned out of the region-of-interest. In other embodiments, the frame includes a substance selected from a list of substances consisting of carbon and organic polymer. In yet other embodiments, the patient is positioned on a table, and the location pad is configured to be positioned between the patient and the table.

In an embodiment, at least one of the field-generators includes multiple non-concentric coils. In another embodiment, at least one of the field-generators includes multiple concentric coils.

There is additionally provided, in accordance with an embodiment of the present invention, a method for producing a location pad, the method includes providing multiple field-generators for generating respective magnetic fields in a region-of-interest of a patient organ, so as to measure a position of a medical instrument in the region-of-interest. The multiple field-generators are fixed on a frame at respective positions surrounding the region-of-interest, and the frame is transparent to X-ray radiation, at least at the region-of-interest.

There is further provided, in accordance with an embodiment of the present invention, a method including positioning a location pad relative to a region-of-interest of a patient, the location pad includes a frame that fixes multiple field-generators at respective positions surrounding the region-of-interest, and the frame is transparent to an X-ray radiation at least at the region-of-interest. A medical instrument is inserted into the region of interest. A position of the medical instrument is tracked using the field-generators. Simultaneously with the position tracking, the region-of-interest is irradiated with a fluoroscopic imaging system, so as to produce an image of the region-of-interest.

The present disclosure will be more fully understood from the following detailed description of the embodiments thereof, taken together with the drawings, in which:

DETAILED DESCRIPTION OF EMBODIMENTS

Overview

Figure 1:
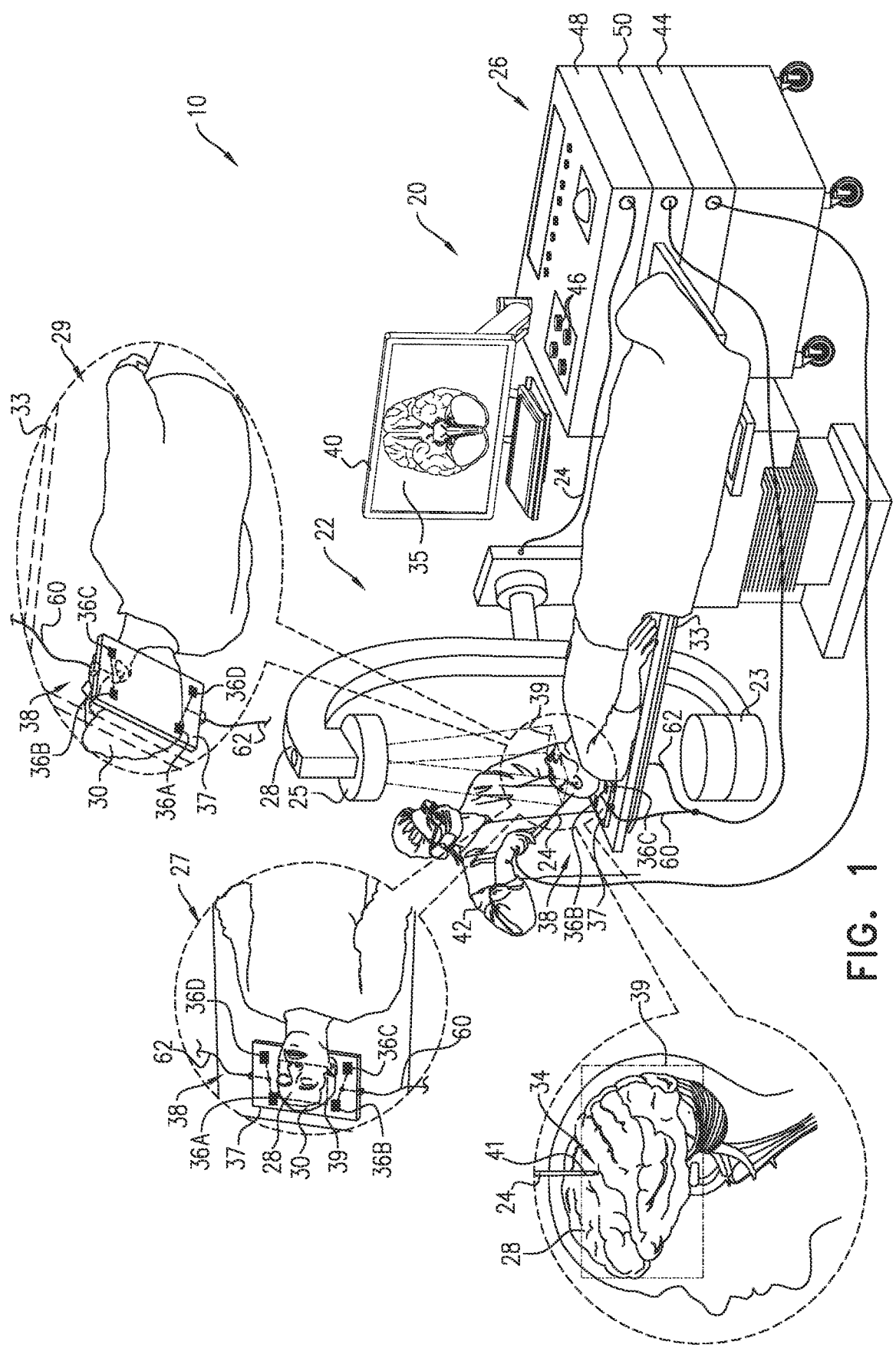
FIG. 1 is a schematic pictorial illustration of a neurosurgical system, in accordance with an embodiment of the present invention.

Medical instruments and guidewires are used in various therapeutic and diagnostic medical procedures, such as in neurosurgery.

Embodiments of the present invention that are described hereinbelow provide methods and apparatus for improving anatomical imaging and simultaneously tracking medical instruments during neurosurgical procedures.

In neurosurgical procedures carried out using a neurosurgical system, a surgeon may insert a guidewire into the patient head and may navigate the guidewire to the target region in the patient brain for performing the neurosurgical procedure.

In some embodiments, the neurosurgical system may comprise a magnetic position tracking subsystem, which is configured to track the position of the guidewire in the patient head. In some embodiments, the magnetic position tracking subsystem comprises multiple field-generators that are typically fixed on a location pad, and are configured to apply respective magnetic fields to a region-of-interest (ROI) at the patient head. In some embodiments, the magnetic position tracking subsystem comprises a position sensor, typically installed at the distal end of the guidewire. The position sensor is configured to produce, in response to the magnetic fields, a position signal indicative of the position and orientation of the distal end within the patient head.

In some embodiments, the position tracking subsystem comprises a processor, which is configured to display, based on the position signal, a position of the distal end overlaid on an anatomical image of the patient head.

In some scenarios, it is desirable to apply a fluoroscopic system simultaneously with the magnetic position tracking system. For example, in order to acquire an X-ray image, also referred to herein as a fluoroscopic image, of the ROI of the patient head or of any other organ in question. In a neurosurgical procedure, parts of the location pad may fall within the irradiated volume of the fluoroscopic system, and may block or obstruct portions of the fluoroscopic image of the patient brain.

In some embodiments, the location pad comprises a frame that is transparent to the X-ray radiation, also referred to herein as "fluoro-transparent," at least at the ROI. The fluoro-transparent frame is configured to fix the field-generators thereon, at respective positions surrounding the ROI. The transparency of the frame to the X-ray radiation causes little or no obstruction to the fluoroscopic imaging, at least in fluoroscopic projections that are commonly used in neurosurgical procedures.

In some embodiments, the location pad may comprise field-generators having non-concentric coils arranged so as to enable a low profile location pad. Such a location pad can be easily placed between a moving table, on which the patient is positioned, and the patient head, as opposed to conventional location pads that are thicker and have to be placed below the table. In other embodiments, at least one of (and typically all) the field-generators may comprise concentric coils. This configuration may be used in case the low profile location pad is not necessary, or for enhancing the functionality of the location pad.

The disclosed techniques improve the quality of neurosurgical procedures by enabling simultaneous imaging and treatment of the brain during surgical or any other invasive procedures. Moreover, the disclosed techniques may be applied, mutatis mutandis, to medical procedures carried out on other organs of the patient body.

System Description

FIG. 1 is a schematic pictorial illustration of a neurosurgical system 10, in accordance with an embodiment of the present invention. In some embodiment, neurosurgical system 10 comprises a fluoroscopic imaging subsystem 22, which is configured to irradiate X-rays to an organ in question, and a magnetic position tracking subsystem 20 described in detail below.

Reference is now made to an inset 32. In some embodiments, during a neurosurgical procedure, a surgeon 42 navigates any suitable type of a guidewire 24, into a brain 28 of a patient 30. In some embodiments, a position sensor 41 is coupled to a distal end 34 of guidewire 24.

In some embodiments, surgeon 42 navigates distal end 34 to a target location within a region-of-interest (ROI) 39 of brain 28, and subsequently, applies a medical device (not shown) typically guided along guidewire 24 to distal end 34, so as to carry out a medical procedure in ROI 39, e.g., tumor removal.

Reference is now made to an inset 27. In some embodiments, neurosurgical system 10 comprises a low-profile location pad 38 placed below the head of patient 30. Location pad 38 comprises field-generating coils, referred to herein as field-generators 36A-36D that are mounted on a frame 37 around ROI 39.

In some embodiments, frame 37 is transparent to X-rays, such that X-rays irradiated by an X-ray source 23 of subsystem 22, pass through pad 38 and brain 28, and sensed by an X-ray detector 25. Note that frame 37 has a low-profile (e.g., thickness of about 1.2 cm) and X-ray detector 25 is configured to output electrical signal indicative of the sensed X-rays for producing an anatomical image 35 of at least a section of ROI 39, as will described below.

In some embodiments, location pad 38 further comprises electrical cables 60 and 62 configured to electrically couple between field-generators 36A-36D and a driver circuit 50 of magnetic position tracking subsystem 20. Location pad 38 is described in more detail in FIG. 2 below.

In the context of the present disclosure, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In some embodiments, neurosurgical system 10 comprises an operating console, referred to herein as a console 26 for brevity. Console 26 comprises a processor 44, driver circuit 50, interface circuitry 48 to fluoroscopic imaging subsystem 22, input devices 46, and a display 40. In the exemplary configuration of FIG. 1, pad 38 comprises four field-generators 36A-36D, in other embodiments, pad 38 may comprise any other suitable number of field-generating coils.

In some embodiments, position sensor 41 is configured to sense magnetic fields generated by field-generators 36A-36D and to transmit, to processor 44, electrical signals indicative of the position and orientation of distal end 34 in ROI 39.

Magnetic position tracking subsystem 20 may be implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Publication 2002/0065455 A1, issued as U.S. Pat. No. 6,690,963 on Jan. 10, 2004; U.S. Patent Publication 2003/0120150 A1, issued as U.S. Pat. No. 7,729,742 on Jun. 1, 2010; and U.S. Patent Publication 2004/0068178 A1, now abandoned, whose disclosures are all incorporated herein by reference.

Reference is now made to an inset 29. In some embodiments, location pad is positioned on top of a table 33 and under the patient head, such that generators 36A-36D are located at fixed, known positions external to patient 30. Driver circuit 50 is configured to drive field-generators 36A-36D with suitable signals so as to generate the aforementioned magnetic fields in a predefined volume around ROI 39 of brain 28.

In some embodiments, at least one of field-generators 36A-36D may comprise three non-concentric coils arranged and packaged in a low profile field-generator. Each coil is thus configured to generate a magnetic field component in one direction out of three mutually-orthogonal directions. In this configuration two of the coils are positioned side-by-side in a given plane, and the third coil is wound around the two coils in the given plane so as to obtain the low profile field-generator. This configuration is described in detail in U.S. Patent application publication 2017/0007155, now abandoned, whose disclosure is incorporated herein by reference.

In other embodiments, at least one of field-generators 36A-36D may comprise three concentric coils. Such configuration, however, typically results in a thicker field-generator. Note that typically all field-generators 36A-36D have the same configuration, and the arrangement of the coils is determined based on various parameters, such as but not limited to the specified thickness of the location pad. In the example of neurosurgery the thickness may not be critical, and therefore both configurations may be applicable. Note that location pad 38 may comprise any suitable number of field-generators, other than four.

In some embodiments, an operator of neurosurgical system 10 may produce anatomical image 35 by operating subsystem 22 using input devices 46 and a suitable graphical user interface (GUI), and processor 44 is configured to display anatomical image 35 on display 40. In some embodiments, processor 44 is further configured to receive, from position sensor 41, a position signal indicative of the position of distal end 34 in brain 28. Based on the position signal, processor 44 is configured to display (a) the position of distal end overlaid on anatomical image 35, and (b) a frame, indicative of the position of ROI 39, so that an operator of subsystem 22 may adjust the direction of the irradiated X-rays on the head of patient 30.

This particular configuration of neurosurgical system 10 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of surgical systems, and particularly, to other sorts of position tracking systems applied in conjunction with imaging systems or subsystems, such as but not limited to, fluoroscopic-based, or computerized tomography (CT)-based systems or subsystems.

Location Pad Transparent to X-Ray Radiation

Figure 2:
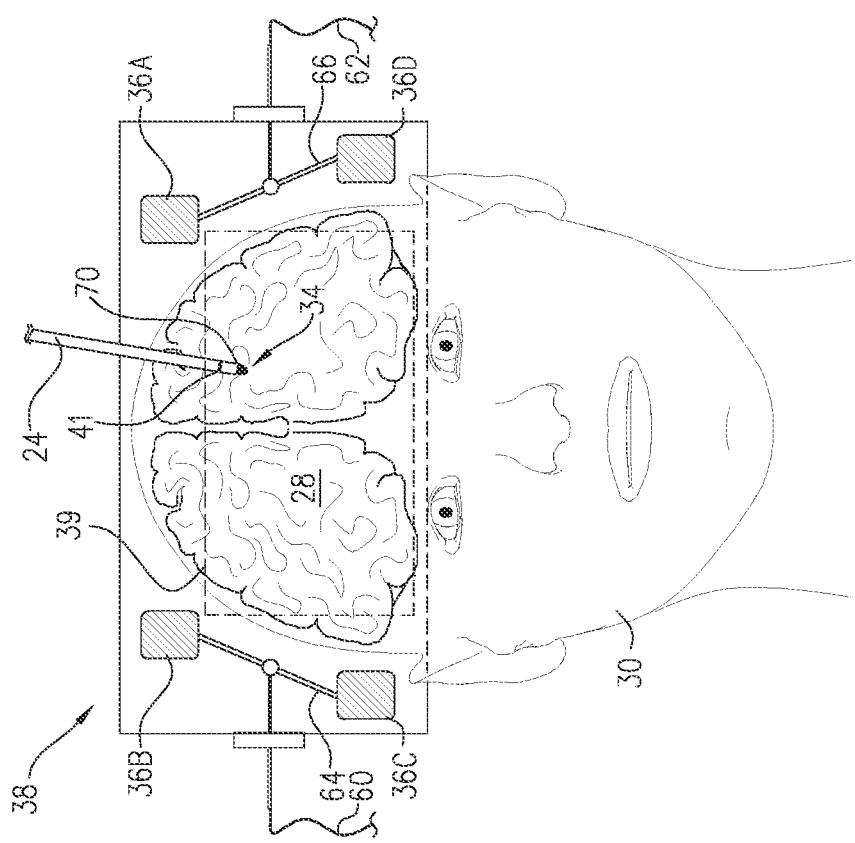
FIG. 2 is a schematic top-view of a fluoro-transparent location pad, in accordance with an embodiment of the present invention.

FIG. 2 is a schematic top-view of location pad 38, in accordance with an embodiment of the present invention. In some embodiments, frame 37 comprises a rigid substance that is transparent to X-rays, such as but not limited to carbon film, carbon fiber and various types of organic polymers (e.g., plastic).

In some embodiments, field-generators 36A and 36D are fixed at one side of frame 37 using a fixing device 66, and are electrically connected to driver circuit 50 via electrical cable 62. Similarly, field-generators 36B and 36C are fixed at the opposite side of frame 37 using a fixing device 64, and are electrically connected to driver circuit 50 via electrical cable 60. In such embodiments, field-generators 36A-36D, fixing devices 64 and 66, and electrical cables 60 and 62, are all fixed on frame 37 outside ROI 39, as shown in FIG. 2.

In some embodiments, fixing devices may be movable to other locations on the surface of frame 37, so as to set the size and shape of ROI 39.

In other embodiments, frame 37 is configured to fix field-generators 36A-36D at respective positions surrounding ROI 39. In such embodiments, field-generators 36A-36 may be attached on frame 37 using any suitable technique, such as but not limited to gluing, welding, soldering, or screwing. Note that in this configuration, fixing devices 64 and 66 may be removed from location pad 38.

In some embodiments, field-generators 36A-36D are configured to generate respective magnetic fields in ROI 39 of patient brain 28 so as to measure the position of distal end 34 in ROI 39. In such embodiments, when surgeon 42 is positioning distal end 34 at a position 70 within brain 28, processor 44 is receiving from position sensor 41 a position signal indicative of position 70, and overlays position 70 on anatomical image 35.

In some embodiments, surgeon 42 may use guidewire 24 for positioning any suitable medical instrument for performing the medical procedure. Additionally or alternatively, In other embodiments, surgeon 42 may use the same techniques for positioning, at a target position within brain 28, any other neurosurgical-related medical device having position sensor 41 coupled to its distal end. In such embodiments, guidewire 24 may be removed from the configuration of neurosurgical system 10.

Simultaneous Imaging and Position Tracking
During A Neurosurgical Procedure

Figure 3:
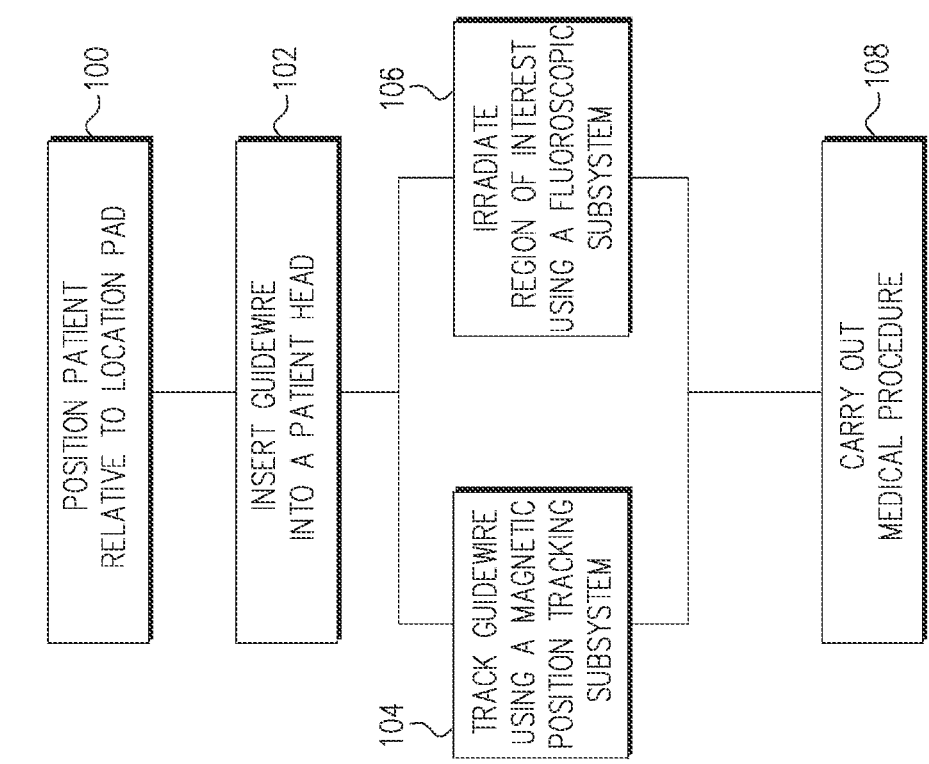
FIG. 3 is a flow chart that schematically illustrates a method for simultaneous imaging and position tracking during a neurosurgical procedure, in accordance with embodiments of the present invention.

FIG. 3 is a flow chart that schematically illustrates a method for simultaneous imaging and position tracking during a neurosurgical procedure, in accordance with embodiments of the present invention.

The method begins at a patient positioning step 100, with positioning patient 30 on table 33, relative to location pad 38, such that location pad 38 is positioned between table 33 and the patient head. At a guidewire insertion step 102, surgeon 42 inserts guidewire 24 into the head of patient 30.

At a tracking step 104, which is carried out during the neurosurgical procedure, surgeon 42 may apply magnetic position tracking subsystem 20 for tracking distal end 34. In such embodiments, surgeon 42 may use console 26 for controlling driver circuit 50 to apply the aforementioned magnetic fields to ROI 39, and further controls position sensor 41 and processor 44 for tracking the position of distal end 34 in brain 28 and for displaying the position overlaid on anatomical image 35. At an irradiation step 106, which is carried out in parallel to tracking step 104, surgeon 42 may apply subsystem 22 for irradiating ROI 39 of brain 28. Note that the structure of location pad 38 enables simultaneous imaging of ROI 39 and position tracking of distal end 34 within ROI 39.

At a medical procedure conducting step 108, surgeon 42 conducts the neurosurgical procedure based the displayed position of distal end 34 overlaid on anatomical image 35. Note that step 108 typically terminates the method of FIG. 3, however, surgeon may apply steps 104 and 106 simultaneously to carry out additional activities related to the procedure, such as but not limited to retracting distal end 34 out of the head of patient 30.

Although the embodiments described herein mainly address neurosurgical procedures, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A location pad, comprising:
   (a) multiple field-generators, which are configured to generate respective magnetic fields in a region-of-interest of a patient organ, for measuring a position of a medical instrument in the region-of-interest;
   (b) a frame, which is configured to fix the multiple field-generators at respective positions surrounding the region-of-interest; and
   (c) a fixing assembly associated with both the multiple field-generators and the frame, wherein the fixing assembly is configured to allow the multiple field-generators to move to multiple locations of a surface of the frame in order to adjust the size and shape of the region-of-interest.

2. The location pad according to claim 1, wherein the field-generators comprise at least first and second field-generators, and comprising at least a first electrical cable connected to the first field-generator, and a second electrical cable connected to the second field-generator, and wherein the first and second electrical cables are positioned out of the region-of-interest.

3. The location pad according to claim 1, wherein the frame comprises a substance selected from a list of substances consisting of carbon and organic polymer.

4. The location pad according to claim 1, wherein the patient is positioned on a table, and wherein the location pad is configured to be positioned between the patient and the table.

5. The location pad according to claim 1, wherein at least one of the field-generators comprises multiple non-concentric coils.

6. The location pad according to claim 1, wherein at least one of the field-generators comprises multiple concentric coils.

7. A method for producing a location pad, the method comprising:
   (a) providing multiple field-generators for generating respective magnetic fields in a region-of-interest of a patient organ, so as to measure a position of a medical instrument in the region-of-interest;
   (b) utilizing a fixing assembly to adjust the spatial positioning of the multiple field-generators in order to set the size and shape of the region-of-interest; and
   (c) fixing the multiple field-generators on a frame at respective positions surrounding the region-of-interest.

8. The method according to claim 7, wherein the field-generators comprise at least first and second field-generators, and comprising connecting a first electrical cable to the first field-generator, and a second electrical cable to the second field-generator, and positioning the first and second electrical cables out of the region-of-interest.

9. The method according to claim 7, wherein at least one of the field-generators comprises multiple non-concentric coils.

10. The method according to claim 9, and comprising arranging at least two of the non-concentric coils side-by-side in a given plane.

11. The method according to claim 7, wherein at least one of the field-generators comprises multiple concentric coils.

12. The method according to claim 7, wherein the frame comprises a substance selected from a list of substances consisting of carbon and organic polymer.

13. A method, comprising:
   (a) positioning a location pad relative to a region-of-interest of a patient, wherein the location pad comprises a frame that fixes multiple field-generators at respective positions surrounding the region-of-interest;
   (b) adjusting the spatial position of the multiple filed-generators utilizing a fixing device of the frame in order to set the size and shape of the region-of-interest;
   (c) inserting a medical instrument into the region of interest;
   (d) tracking a position of the medical instrument using the field-generators; and
   (e) simultaneously with tracking the position, irradiating the region-of-interest with a fluoroscopic imaging system so as to produce an image of the region-of-interest.

14. The method according to claim 13, wherein positioning the location pad comprises placing the location pad between the patient and a table on which the patient is positioned.

15. The method according to claim 13, wherein tracking the position comprises producing magnetic fields using the field-generators, and tracking the position by applying magnetic position tracking to the produced magnetic fields.

16. The method according to claim 13, wherein the region-of-interest comprises at least a volume of a brain of the patient, and wherein inserting the medical instrument comprises inserting a guidewire for performing a neurosurgical procedure at the region of interest.

17. The method according to claim 13, wherein the location pad comprises a low profile.

18. The method of claim 13, wherein the multiple field-generators comprises concentric coils.

19. The method of claim 13, wherein the medical instrument comprises a guidewire.

20. The method of claim 13, wherein the medical instrument comprises a position tracking sensor.

* * * * *